Figure 3:
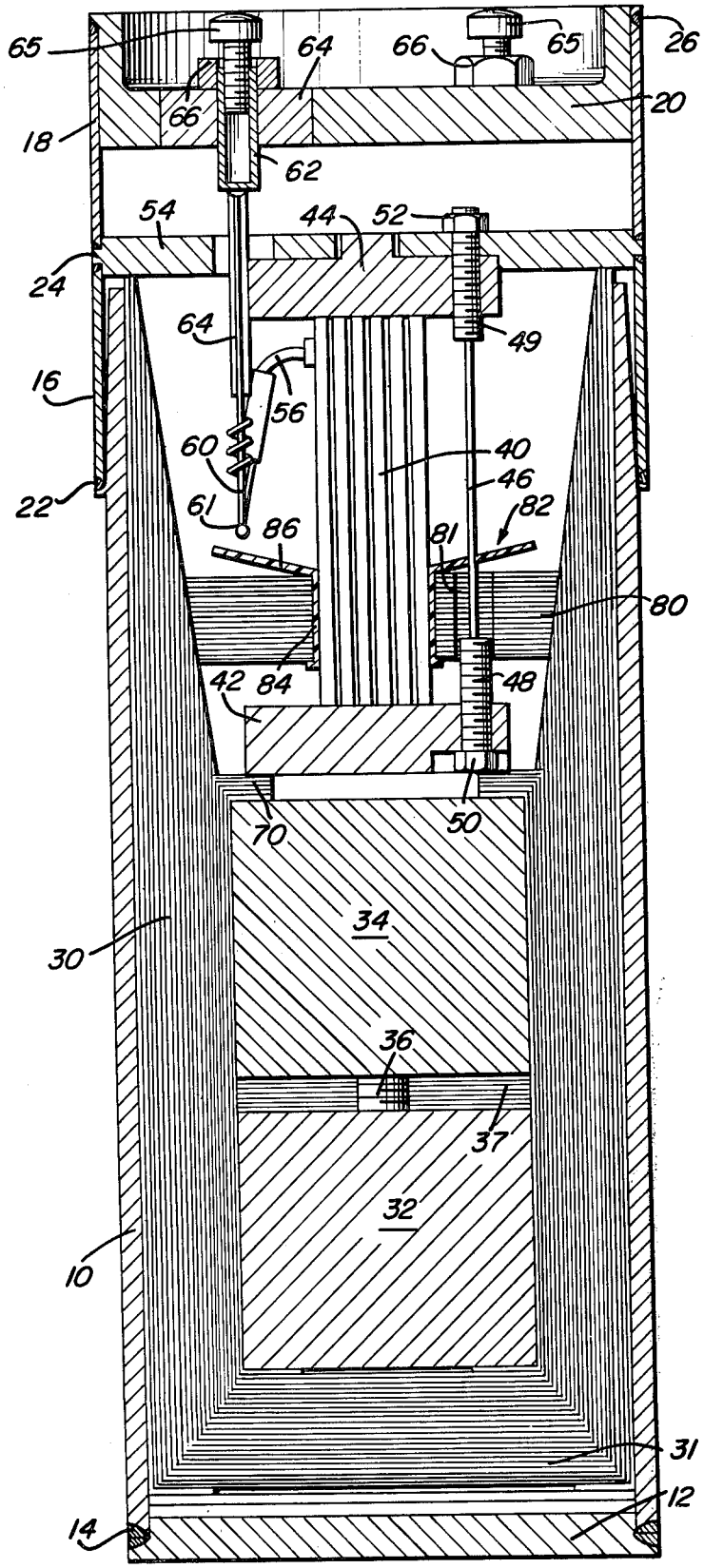

United States Patent [19]

Barr

[11] 4,073,665
[45] Feb. 14, 1978

[54] MICROWATT THERMOELECTRIC GENERATOR

[75] Inventor: Harold N. Barr, Baltimore, Md.

[73] Assignee: Nuclear Battery Corporation, Columbia, Md.

[21] Appl. No.: 734,127

[22] Filed: Oct. 20, 1976

Related U.S. Application Data

[63] Continuation of Ser. No. 489,737, July 18, 1974, abandoned.

[51] Int. Cl.² .................. H01L 35/02; G21H 1/10
[52] U.S. Cl. .............................. 136/202; 252/181.4
[58] Field of Search ............... 136/202; 252/181.4, 252/181.6

[56] References Cited

U.S. PATENT DOCUMENTS

| | | |
|---|---|---|
| 3,357,866 | 12/1967 | Belofsky ........................ 136/202 |
| 3,842,489 | 10/1974 | Bustard ...................... 136/202 X |

*Primary Examiner*—Maynard R. Wilbur
*Assistant Examiner*—Richard E. Berger
*Attorney, Agent, or Firm*—Fleit & Jacobson

[57] ABSTRACT

A microwatt thermoelectric generator suitable for implanting in the body. The disclosed generator utilizes a nuclear energy source. Provision is made for temporary electrical connection to the generator for testing purposes, and for ensuring that the heat generated by the nuclear source does not bypass the pile. Also disclosed is a getter which is resistant to shrinkage during sintering, and a foil configuration for controlling the radiation of heat from the nuclear source to the hot plate of the pile.

4 Claims, 4 Drawing Figures

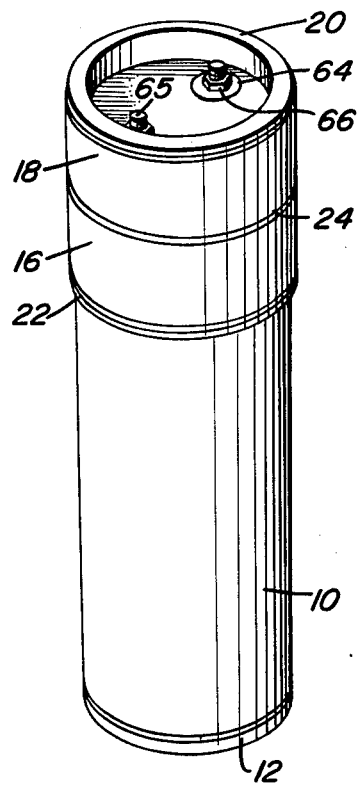
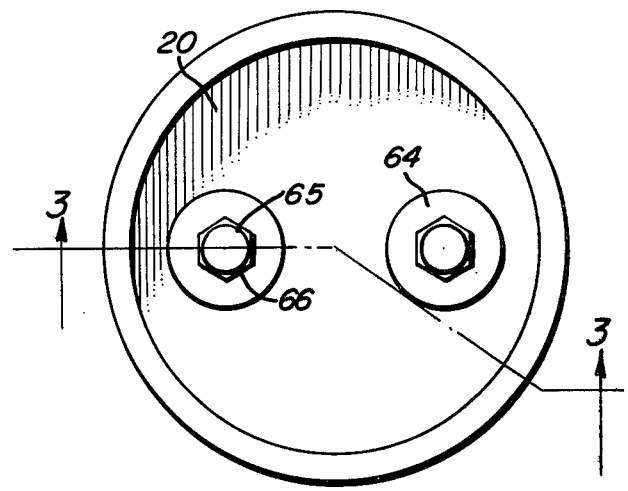
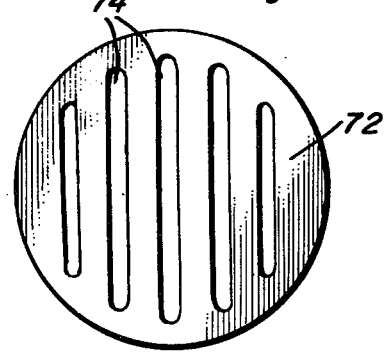

MICROWATT THERMOELECTRIC GENERATOR

This is a continuation of application Ser. No. 489,737, filed July 18, 1974, now abandoned.

The present invention relates to an improved microwatt thermoelectric generator of the type described in commonly assigned U.S. Patent Application Ser. No. 189,842, filed Oct. 18, 1971, for MICROWATT THERMOPLASTIC GENERATORS, now abandoned in favor of continuation Application Ser. No. 530,948, filed Dec. 9, 1974.

In Assignee's earlier application, a highly advantageous microwatt thermoelectric generator construction is disclosed which has special applicability for powering implants within a human body such as those used to control or regulate heart function. For the first time, an electrical power supply utilizing a nuclear energy source was made available for this purpose.

The object of the present invention is to provide an improvement to the construction disclosed in Assignee's co-pending earlier application, which increases the efficiency and life of the generator. According to this invention the improvement constitutes a unique construction for the barium getter enabling same to maintain its shape and configuration during processing to eliminate shrinkage. According to the prior design, a pressed barium pellet was contained within a tantalum can and processed by heating which had the result that the barium pellet would be activated but also would shrink. As a result of this shrinkage, once in use, the barium pellet would not fit tightly in the can and hence rattled. Besides being disconcerting to the user, the fact that the pellet was loose in the can and could move, resulted in the possibility of damaging the foil insulation package through impact. According to the present invention this problem was solved by using a tungsten fiber composite as a mass in which to contain the barium. By this novel technique, pellet formation and subsequent processing was carried out without the barium shrinking and therefore the final getter structure occupies the entire volume of the tantalum can.

The foregoing object and advantage of the present invention will become more evident from the following detailed description of th drawings in which FIG. 1 is a perspective view showing the generator of the present invention, FIG. 2 is a top plan of the generator shown in FIG. 1, FIG. 3 is a view in section taken along line 3—3 of FIG. 2, and FIG. 4 is a view in plan showing an alternate foil grid.

Referring to the drawing, the improvement of the present invention is shown in detail. The microwatt thermoelectric generator according to the Assignee's earlier copending application consists in general of a cylindrical outer casing 10 which is closed at one end by means of plate 12 through the intermediary of a weld joint 14 and at its other end by means of shells 16, 18 and header 20 which are welded together by means of weld joints 22, 24 and 26 as indicated in the figures. The casing 10 contains a foil insulation package 30 including a lower foil package 31, constructed as described in the earlier application.

Located within the foil insulation package 30 is a nuclear source 32 containing a small quantity of plutonium oxide and a getter 34 consisting of a perforated tantalum can containing processed barium contained in a tungsten wire matrix. To prepare the getter 34, barium powder is mixed with a mass of approximately 15% by weight, 0.1 inch long, one mil diameter pieces of tungsten wire. After mixing, the wire-barium mass is pressed into pellets and placed in cans and processed as described in Assignee's earlier application. The presence of the tungsten wires reinforces the mixture against shrinkage during the sintering process. Other materials than tungsten could be used, so long as compatible with barium.

The container for the nuclear source 32 is coupled in contact with the tantalum can of the getter 34 by means of a stud 36. Gold foils 37 are interposed between source 32 and getter 34 to assure a tight fit and good thermal contact. As will be evident, the foil insulation package 30 is fabricated to accommodate the nuclear source 32 and the getter 34.

The container 10 also houses a thermopile 40 having a hot plate 42 at one end and a cold plate 44 at its other end, both of which are insulated from the pile itself by an oxide coating or the like as described in the earlier application. Also, the details of the pile as regards its construction and electrical connections are all described in the earlier application. The hot and cold plates 42 and 44 bear against the pile 40 with a force determined by a number of tension wires 46 which are maintained in tension between studs 48 and 49 passing through bores in hot plate 42 and cold plate 44, respectively. The ends of each tension wire 46 are fastened to the studs 48 and 49 in a conventional manner and the ends of the studs remote from the pile receive thereon nuts 50 and 52, respectively, for the purpose of drawing the desired tension on the wire 46. Although only one wire 46 is shown, it should be appreciated that the tension forces are preferably evenly spaced about the pile 40, and that any convenient number of tension wires may be used.

The cold plate 44 is received within a heat transfer plate 54 which fits within the shells 16 and 18 with a close tolerance and is fixed to shells 16 and 18 by weld 24. The foil insulation package 30 between the hot plate 42 and the end of the pile 40 attached to the cold plate 44 is tapered as shown in the drawing.

The electrical output from the pile 40 is obtained via leads 56 which connect with wires 60 by means of suitable joints 62. Wires 60 extend through bores defined in the heat transfer plate 54 and are soldered to the closed ends of niobium tubes 62. Insulating sleeves 64 protect wires 60 from contact with the plate 54. The niobium tubes 62 are fitted into feed-through assemblies in header 20 which are formed according to the description in the earlier application and include alumina sleeves 64 brazed into openings in the tantalum or niobium header 20 and into which the niobium tubes themselves are brazed. Stainless steel nuts 66 are brazed onto the exterior of niobium tubes 62 and project above the open ends of the tubes 62. Stainless steel bolts 65 are threaded into the open ends of tubes 62 and coact with nuts 66 to enable temporary attachment of leads for test purposes. After testing, permanent attachment is made by soldering to nuts 66.

Interposed between hot plate 42 and getter 34 is a foil separator package 70 consisting of approximately 30 annular foils, each being on the order of one mil thick, having an inside opening or diameter of about 0.25", and an outside diameter of about 0.35". This foil separator package serves to isolate the getter 34 and heat source 32 from the pile 40 whereby the hot plate 42 of the pile operates at about 200° F., whereas the getter 34 operates in excess of 400° F. Also, the presence of the insulating foil separator package 70 between the hot plate 42 and the getter 34, serves to maintain the spacing between these elements. A rigid mechanical connection is therefore not required.

FIG. 4 shows a modification for an element of the foil separator package 70 which utilizes, in place of annular foils, disc foils 72 defining an array of cutouts 74 to establish a grid. When the foil separator package 70 is comprised of 30 foil grids 72, the amount of radiation possible away from the getter 34 to the hot plate 42 is materially reduced and the getter 34 will run about 50° F. hotter, materially increasing its gettering efficiency.

Interposed between the hot plate 42 and the cold plate 44 is an upper foil package 80 consisting of a large number of annular foils stacked on an annular plastic insulator 82 having a central hub 84 rectangular in configuration which fits about the pile 40 and an integral flange 86. The foils of the package 80 are stacked on the hub 84 and extend in a lateral sense outwardly to contact the tapered surface of the foil insulating package 30. Each foil element of the upper foil package 80 is provided with holes 81 through which tension wires 46 can freely pass. The insulating upper foil package 80 is located closer to the hot plate 42 than the cold plate 44, and prevents heat from bypassing the pile 40. Utilizing the upper foil package 80, it is possible to shorten the pile 40 by approximately ⅛" and still obtain higher efficiency. This size reduction is substantial, since the overall length of the pile is only about ½", with the entire generator being less than 2" long.

It will be appreciated from Assignee's earlier copending application that the interior of the casing 10 is maintained under high vacuum conditions in order that the foil insulation package 30 operates effectively. Consequently, getter 34 must perform as efficiently as possible to prevent any loss in vacuum and thereby prevent heat loss through the insulation. As indicated earlier, the temperature of getter 34 must be maintained at the highest possible value consistent with the hot plate 42 of the pile being at approximately 200° F. There is approximately a 100° F. temperature drop across the pile so that the cold end of the pile or cold plate 44 operates at approximately 100° F., close to body temperature.

Although the present invention has been shown and described with reference to a preferred embodiment, nevertheless, changes in the configuration which do not depart from the spirit on the teachings hereof are deemed to come within the purview of the inventive concept.

What is claimed is:

1. In a microwatt thermoelectric generator including a sealed container having a feed-through assembly for making external electrical connection to the interior of the sealed container, a thermopile having a cold end and a hot end located within the sealed container with its cold end adjacent to the feed-through assembly and electrically connected therewith, a nuclear source located adjacent the hot end of the thermopile to furnish heat thereto, a foil insulation package located within the sealed container surrounding the thermopile and nuclear source, and getter means located within said foil insulation package, the improvement of the getter means comprising gas permeable container means containing a sintered mass of barium particles having distributed therethrough thin filler wire.

2. The microwatt thermoelectric generator of claim 1 wherein the thin filler wire is approximately 0.1 inch long and one mil in diameter and constitutes 15% by weight of the mass.

3. The microwatt thermoelectric generator of claim 1 wherein the thin filler wire is tungsten.

4. The microwatt thermoelectric generator of claim 1 wherein the container means is a tantalum can.

* * * * *